United States Patent [19]

Cordier et al.

[11] Patent Number: 4,892,976

[45] Date of Patent: Jan. 9, 1990

[54] PROCESS FOR THE PREPARATION OF ALDEHYDES

[75] Inventors: Jean Cordier, Saint Saul·e; Bernard Dussart, Schiltigheim; Francis Petit; Yves Castanet, both of Villeneuve D'Aso; Serge Melloul, Lille; André Mortreux, Hem, all of France

[73] Assignee: Sollac, Paris, France

[21] Appl. No.: 219,926

[22] Filed: Jul. 15, 1988

[30] Foreign Application Priority Data

Jul. 16, 1987 [FR] France ............................. 87 10044

[51] Int. Cl.$^4$ .............................................. C07C 45/49
[52] U.S. Cl. ................................... 568/465; 568/460; 568/484
[58] Field of Search ............... 568/465, 460, 462, 458, 568/882, 484

[56] References Cited

U.S. PATENT DOCUMENTS

| 4,431,835 | 2/1984  | Gauthier-Lafaye | 568/484 |
| 4,477,685 | 10/1984 | Chan            | 568/484 |
| 4,511,741 | 4/1985  | Wegman et al.   | 568/484 |
| 4,513,151 | 4/1985  | Wegman et al.   | 568/484 |

FOREIGN PATENT DOCUMENTS

| 0046128 | 2/1982 | France | 568/484 |
| 0144340 | 8/1983 | Japan  | 568/484 |
| 0013745 | 1/1984 | Japan  | 568/484 |
| 0104329 | 6/1984 | Japan  | 568/484 |

OTHER PUBLICATIONS

Chemical Abstracts-vol. 101, No. 21, Nov. 1984, p. 698, Abstract No. 191141h.

Primary Examiner—Werren B. Lone
Attorney, Agent, or Firm—Fay, Sharpe, Beall, Fagan, Minnich & McKee

[57] ABSTRACT

The process for the preparation of an aldehyde of formula R—CHO in which R is an alkyl group of $C_1$-$C_7$ comprises according to the invention the reaction on an alkyl formate of formula H—COOR in which R has the meaning given above, of a gas constituted mainly by CO, in the presence of
(a) a catalyst based on a metal chosen from among Rh, Ru, Ir, mixtures of them or a mixture of Rh and/or Ru and/or Ir with Co, Ni or Fe,
(b) a promoter chosen from among iodides and mixtures of covalent compounds of iodine and a phosphine or a tertiary amine,
(c) a solvent consisting of a cyclic N-alkyl amide.

12 Claims, 1 Drawing Sheet

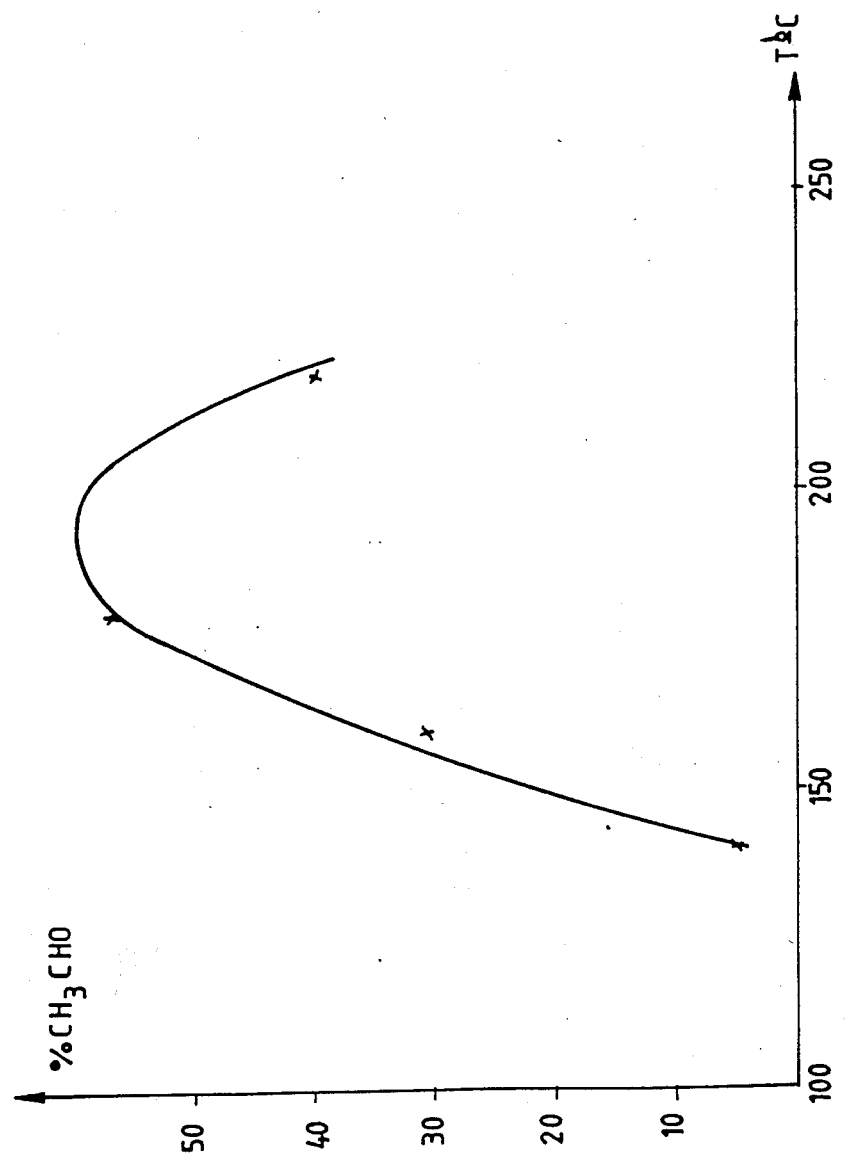

PROCESS FOR THE PREPARATION OF ALDEHYDES

The present invention relates to a process for the preparation of aldehydes from alkyl formates and, in particular, of acetaldehyde from methyl formate.

The hydrocarbonylation of methanol to give acetaldehyde ($CH_3CHO$) is a well-known reaction. It is catalysed by transition metals (cobalt alone or in synergy with other metals . . . ) very often co-ordinated by a ligand of the $ER_3$ type (E=P, As, Sb . . . , R=an organic radical). The reaction scheme is as follows:

$$CH_3OH + CO + H_2 \rightarrow CH_3CHO + H_2O$$

The selectivity for acetaldehyde is never complete, a variable but significant fraction being hydrogenated to ethanol according to the scheme $$CH_3CHO + H_2 \rightarrow CH_3CH_2OH$$

A process was described in DE-C-20 26 031 for the preparation of a carboxylic acid from an alkyl formate in the presence of a catalyst such as Co, Ni or Fe and possibly a halogen or a halide in certain proportions in various solvents, including N-methylpyrrolidone. This process leads, however, to the formation of acetic acid. Moreover, a similar process has been described in U.S.- 4 194 056 in which a rhodium salt is used as catalyst. The reaction is preferably carried out in the absence of solvent and leads to the formation of acetic acid.

The aim of the present invention is to provide a process for the preparation of aldehydes with good selectivity by reaction of a gas constituted mainly of CO on an alkyl formate.

The subject of the present invention is thus a process for the preparation of an aldehyde of formula $$R-CHO$$

in which R is an alkyl group of $C_1$-$C_7$, comprising the reaction on an alkyl formate of formula $$H-COOR$$

in which R has the meaning given above, of a gas constituted mainly of CO, in the presence of:

(a) a catalyst based on a metal chosen from among Rh, Ru, Ir, mixtures of them or a mixture of Rh and/or Ru and/or Ir with Co, Ni or Fe, this catalyst being used in a molar proportion of between $10^{-2}$ and $10^{-4}$ with respect to the alkyl formate, (b) a promoter chosen from among the iodides of alkali and alkaline earth metals, quaternary ammonium or phosphonium iodides, and mixtures of covalent compounds of iodine and a phosphine of formula $PR'_3$, $R'$ being an alkyl or aryl group, or a tertiary amine of formula $NR''_3$, $R''$ being an alkyl group, the iodide or the covalent compound of iodine being used in a molar proportion of $4.10^{-2}$ to $0.25.10^{-2}$ with respect to the alkyl formate, (c) a solvent consisting of a cyclic N-(alkyl of $C_1$-$C_6$) amide, the cyclic amide being used in a molar proportion of at least 1 with respect to the alkyl formate.

The reaction is advantageously carried out at a temperature of 150° to 230° C. and preferably between 160° and 200° C. and under a pressure of CO of at least 1 MPa and preferably of at least 5 MPa. In practice, the pressures used vary between 5 and 10 MPa.

The catalyst is preferably based on rhodium, ruthenium or iridium. $RhCl_3.3H_2O$, $Rh_2Cl_2(CO)_4$, $RhCOCl(PPh_3)_2$, $Rh_6(CO)_{16}$, $RhBr_3$, $RhI_3$, $RuCl_3$, $RuO_2$, $IrCl_3$ may be mentioned as examples of catalysts.

As has already been indicated, the reaction is carried out in the presence of an iodine-containing promoter. This promoter may be an alkali metal iodide (LiI, KI, NaI) possibly mixed with chromium hexacarbonyl ($Cr(CO)_6$), an alkaline earth metal iodide, a phosphonium iodide $PPh_3R'''I$ or an ammonium iodide $NR'''_4I$, $R'''$ being an alkyl group of $C_1$-$C_4$.

The iodine-containing promoter may also be a mixture of a covalent compound of iodine and a phosphine or tertiary amine. The covalent compound of iodine may be, in particular, iodine or an alkyl iodide of $C_1$-$C_4$ or hydriodic acid. The phosphine may be a trialkylphosphine or a triarylphosphine such as triphenylphosphine. The molar concentration of phosphine or tertiary amine is advantageously at least equal to the molar concentration of the covalent compound of iodine.

Furthermore, reaction is performed in the presence of a solvent consisting of a cyclic N-(alkyl of $C_1$-$C_6$) amide. N-methylpyrrolidone, N-ethylpyrrolidone and N,N-dimethylimidazolidinone may be mentioned as examples of cyclic N-(alkyl of $C_1$-$C_6$) amides.

It should be emphasized that the nature of the solvent is crucial. In fact, the surprising observation has been made that very satisfactory results are obtained in N-methylpyrrolidone or in other cyclic N-alkyl amides but that reaction does not take place in the presence of pyrrolidone, in which case decomposition of the formate into CO and methanol is observed. Similarly, the reactivity and selectivity for acetaldehyde are much lower in other usual solvents (toluene, DMF . . . ).

The process according to the invention may be implemented by using as the gas constituted mainly of CO, gases exhausted from a steelmaking plant (or converter gas), and this thus provides an opportunity to optimize the use of such gases. A gas produced in steelmaking has, for example, the following composition (in moles %):

| | |
|---|---|
| CO | 74.5% |
| $CO_2$ | 14.1% |
| $H_2$ | 2.0% |
| $O_2$ | 0.2% |
| $N_2$ | 8.3% |
| $H_2S$ | 3 ppm |
| COS | 37 ppm |

The following examples illustrate the process according to the invention.

EXAMPLE 1

0.0295 g ($1.2 \cdot 10^{-4}$ mole) of $RhCl_3.3H_2O$, 0.125 g ($9.3 \cdot 10^{-4}$ mole) of LiI and 5 g ($87.10^{-3}$ mole) of methyl formate dissolved in 50 cm³ of N-methylpyrrolidone (NMP) are introduced into a 100 cm³ autoclave filled beforehand with an inert atmosphere.

The autoclave is heated to 180° C. and when the temperature has stabilized, CO is introduced to a pressure of 5 MPa and the mixture is stirred. The conversion of the methyl formate is monitored by the gas chromatographic analysis of samples taken periodically, time zero being taken as the time when stirring is commenced.

After 6 h, stirring is stopped and the autoclave is rapidly cooled.

The liquid and gaseous phases are analysed by means of gas chromatography.

The following results were obtained.

Liquid phase: methanol: 2.75%, acetaldehyde: 42.7%, methyl formate: 49%, ethanol: 1.1%, acetone: 3.4%, butanol: 0.9%.

Gaseous phase: $CO_2 = 11.7\%$, $CH_4 = 4.2\%$, $CO = 85\%$.

The results obtained in example 1 together with other results (examples 2 to 17 obtained by using the same experimental procedure are presented in Table I below. Also shown are the results obtained in comparative examples 1 and 2 in which the procedure was carried out using toluene and pyrrolidone as solvent, respectively, as well as those in comparative examples 3 to 6 in which other variables were modified.

TABLE I

| Example no | Experimental conditions | Time (h) | CH₃OH | CH₃CHO | HCOOCH₃ | C₂H₅OH | CH₃COCH₃ | AcOMe | Butanal | CH₃COOH |
|---|---|---|---|---|---|---|---|---|---|---|
| 1 | T = 180° C. — P_CO = 5 MPa<br>LiI = 0,93 mmole<br>HCOOCH₃ = 87 mmoles<br>RhCl₃, 3H₂O = 0,125 mmole<br>NMP = 50 cm³ | 6 | 2.75 | 42.7 | 49 | 1.1 | 3.4 | — | 0.9 | |
| 2 | T = 160° C. — P_CO = 12 MPa<br>I₂ = 0,25 mmole<br>PPh₃ = 0,7 mmole<br>RhClCO(PPh₃)₂ = 0,125 mmole<br>HCOOCH₃ = 52 mmole<br>NMP = 50 cm³ | 15 | 2.1 | 39 | 55.5 | 0.5 | 0.5 | — | 0.9 | |
| 3 | T = 180° C. — P_CO = 14 MPa<br>other conditions identical no 2 | 2 | 0.5 | 25.3 | 70 | 0.5 | 2.2 | — | 2.2 | |
| 4 | T = 210° C. — P_CO = 14 MPa<br>PPh₃ = 1,4 mmole<br>other conditions identical no 3 | 16<br>2 | 0.5<br>0.2 | 62.5<br>67.4 | 6.3<br>19.1 | 1.6<br>0.3 | 6.1<br>6.1 | —<br>— | 10<br>4.3 | |
| 5 | T = 180° C. — P_CO = 5 MPa<br>LiI = 1,9 mmoles<br>RhCl₃, 3H₂O = 0, 125 mmole<br>HCOOCH₃ = 87 mmoles<br>NMP = 50 cm³ | 16<br>2 | 0.2<br>5.7 | 77.9<br>40.2 | 0.3<br>45 | 0.7<br>1.4 | 3.9<br>5.6 | —<br>1.9 | 14.5<br>— | |
| 6 | T = 140° C. — P_CO = 5 MPa<br>other conditions identical no 5 | 6 | 5.8 | 66.4 | 7.9 | 3.2 | 10.8 | 3.7 | 7.7 | |
| 7 | T = 220° C. — P_CO = 5 MPa<br>other conditions identical no 5 | 6 | 1.3 | 5.7 | 91.5 | — | 0.9 | — | 0.25 | |
| 8 | T = 180° C. — P_CO = 5 MPa<br>Rh₂Cl₂(CO)₄ = 0,062 mmole<br>I₂ = 0,25 mmole — PPh₃ = 2 mmoles<br>HCOOCH₃ = 52 mmoles<br>NMP = 50 cm³ | 1 | 18.8 | 37.6 | 24 | 3 | 7 | 3.5 | 1.7 | |
| 9 | T = 180° C. — P_CO = 5 MPa<br>RhCl₃, 3H₂O = 0.125 mmole<br>LiI = 0.95 mmole<br>PPh₃ = 1,65 mmoles<br>HCOOCH₃ = 87 mmoles<br>NMP = 50 cm³ | 6 | 1.43 | 50.4 | 46 | 0.2 | 1.1 | 0.08 | 0.63 | |
| 10 | T = 180° C. — P_CO = 5 MPa<br>RuCl₃ = 0.125 mmole<br>LiI = 1,9 mmoles<br>HCOOCH₃ = 87 mmoles<br>NMP = 50 cm³ | 6<br>3 | 11.3<br>10.2 | 10.1<br>47.3 | 73<br>30.5 | 0.3<br>0.3 | 1.1<br>— | 1.1<br>2.5 | 0.8<br>2.5 | |

TABLE I-continued

| | Experimental conditions | Time (h) | CH₃OH | CH₃CHO | HCOOCH₃ | C₂H₅OH | CH₃COCH₃ | AcOMe | Butanal | CH₃COOH |
|---|---|---|---|---|---|---|---|---|---|---|
| Comparative example 1 | T = 180° C. − P$_{CO}$ = 14 MPa RhCOCl(PPh₃)₂ = 0.125 mmole I₂ = 0.47 mmole PPh₃ = 3.5 mmoles HCOOCH₃ = 52 mmoles toluene = 50 cm³ | 14 | 1.2 | 8.4 | 60.2 | — | — | 30.2 | — | — |
| 2 | T = 180° C. − P$_{CO}$ = 5 MPa RhCOCl(PPh₃)₂ = 0.125 mmole I₂ = 0.47 mmole- PPh₃ = 3.5 mmoles HCOOCH₃ = 87 mmoles pyrrolidone = 50 cm³ | 2 | 63 | — | 32 | — | — | 4 | — | — |
| Example no 11 | T = 180° C, P(CO) = 5 MPa HI = 0.1 cm³ = 1.25 mmole PPh₃ = 1.5 mmole HCOOCH₃ = 52 mmoles RhCl₃ = 0.125 mmole NMP = 50 cm³ | 2 | 9.5 | 20.5 | 70.0 | — | — | — | — | — |
| comparative example 3 | Identical with no. 11 without PPh₃ | 6 | 9.9 | 59.1 | 29.0 | 0.4 | — | — | — | — |
| 4 | Identical with no. 12 except HI = 2.5 mmoles | 2 | 6.7 | 0.4 | 92.8 | — | — | — | — | — |
| | | 5 | 14.7 | 0.5 | 71.5 | 1 | — | 7.7 | — | 5.0 |
| | | 1 | 7.2 | 0.4 | 34.0 | — | — | 21.0 | — | 37.0 |
| | | 2 | 0.5 | 0.0 | 5.4 | — | — | 7.5 | — | 86.0 |
| 5 | Identical with no. 12 except HI = 10 mmoles T = 180° P(CO) = 5 MPa | 3 | 2.1 | 1.2 | 59.0 | — | 28.0 | — | — | 9.0 |
| 6 | LiI = 3.3 mmoles HCOOCH₃ = 0.66 mmole NMP = 10 cm³ | 2 | 5.8 | 25.0 | 58.4 | — | 10 | 0.8 | — | — |
| Example no 12 | T = 180° C. − P(CO) = 5 MPa CH₃PPh₃I = 1 mmole HCO₂CH₃ = 52 mmoles RhCl₂, 3H₂O = 0.125 mmole PPN⁺I⁻* = 1 mmole | 2 | 6 | 31 | 57.1 | — | 3.9 | 2 | — | — |
| 13 | conditions identical No 12 | 1 | 3.5 | 24.8 | 70.5 | — | 1.2 | — | — | — |
| 14 | T = 184° C. − P(CO) = 7 MPa CH₃N(Et)₃I = 2.5 mmoles HCOOCH₃ = 167 mmoles RhCl₃, 3H₂O = 0.125 mmole NMP = 50 cm³ | 4 | 15.4 | 51.8 | 30 | — | 2.8 | — | — | — |
| 15 | T = 180° C. − PCO = 10 MPa LiI = 1 mmole RhCl₃, 3H₂O = 0.125 mmole Dimethyl imidazolidinone = 50 cm³ | 1 | 9.1 | 16.1 | 74 | — | 0.8 | — | — | — |
| 16 | T = 180° C. P(CO) = 10 MPa LiI = 1.1 mmole HCOOCH₃ = 180 mmoles | 1 | | | | | | | | |

TABLE I-continued

| Experimental conditions | Time (h) | Concentration of product in moles % | | | | | | |
|---|---|---|---|---|---|---|---|---|
| | | CH$_3$OH | CH$_3$CHO | HCOOCH$_3$ | C$_2$H$_5$OH | CH$_3$COCH$_3$ | AcOMe | Butanal | CH$_3$COOH |
| RhCl$_3$.3H$_2$O = 0.125 mmole<br>N—ethyl pyrrolidone = 20 cm$^3$<br>T = 180° C. P$_{(CO)}$ = 7 MPa<br>LiI = 1.8 mmole | | | | | | | | |
| 17  HCOOH$_3$ = 135 mmoles<br>IR ClCO(PPh$_3$)$_2$ = 0.125 mmole<br>NMP = 20 cm$^3$ | 1 | 10 | 23.5 | 66.5 | — | — | — | |

*PPN$^+$I$^-$ bis(triphenyl phosporanylidene) ammonium iodide

The comparative example 1 demonstrates how crucial is the nature of the solvent.

Moreover, the trial experiments performed using HI as promoter have shown that in the absence of PPh$_3$ (comparative examples 3, 4 and 5) reactivity is very low whereas it is significant in the presence of PPh$_3$ (example 11). These trial experiments also show that, in the absence of PPh$_3$ and in the presence of high concentrations of HI (comparative example 5), the product obtained is essentially acetic acid (as is pointed out in DE-C-20 26 031).

Finally, the comparative example 6 shows that a low concentration of N-methylpyrrolidone gives rise mainly to methyl acetate and acetic acid, and not to acetaldehyde.

EXAMPLE 18

The same experimental procedure was used as in example 1 but under the following conditions: methyl formate=5 cm$^3$ (87 mmoles), Rh=0.12 mmole, LiI=3 mmoles, Pco=8 MPa, reaction time: 3 hours.

The concentration in mole % of acetaldehyde was studied as a function of temperature. The results are presented in FIG. 1. This figure demonstrates the crucial effect of temperature and the fact that the highest degree of conversion into acetaldehyde is attained at a temperature of about 180° C.

Under these same conditions, the reaction at higher temperature gives rise to butanal as side product as a result of acetaldehyde undergoing a condensation reaction (cf. Table II).

TABLE II

Influence of temperature on the overall degree of conversion (ODC) and on selectivity.

| Time | T° (°C.) | ODC CH$_3$CHO (%) | Selectivity (%) CH$_3$OH | (butanal) | C$_4$H$_9$OH |
|---|---|---|---|---|---|
| 1 | 160 | 13,5 | 70 | 27 | — |
|   | 180 | 30,5 | 78 | 16 | — |
|   | 220 | 90 | 56 | 24 | 6 |
| 3 | 140 | 4 | 67 | 30 | — |
|   | 160 | 32 | 88 | 9 | — |
|   | 180 | 75 | 82 | 9 | 1,5 |
|   | 220 | 98 | 43 | 24 | 16 |

Conditions: PCO = 5 MPa; LiI = 1,9 mmoles; RhCl$_3$, 3H$_2$O = 0,125 mmole, HCOOCH$_3$ = 87 mmoles, NMP = 50 ml

We claim:

1. A process for the selective preparation of an aldehyde of the formula

R—CHO in which R is a C$_1$-C$_7$ alkyl, the process comprising reacting an alkyl formate of the formula

H—COOR in which R has the meaning given above, with CO in the absence of H$_2$, in the presence of:
(a) a catalyst based on a metal selected from Rh, Ru, Ir, mixtures of them and a mixture of RH and/or Ru and/or Ir with Co, Ni or Fe, said catalyst being used in a molar proportion of between 10$^{-2}$ and 10$^{-4}$ with respect to the alkyl formate;
(b) a promoter selected from the iodides of alkali and alkaline earth metals, quaternary ammonium iodides and phosphonium iodides, mixtures of covalent compounds of iodine and a phosphine of formula PR'$_3$, R' being selected from alkyl and aryl, and mixtures of covalent compounds of iodine and a tertiary amine of formula NR"$_3$, R" being alkyl, the iodide or the covalent compound of iodine being used in a molar proportion of 4·10$^{-2}$ to 0.25·10$^{-2}$ with respect to the alkyl formate; and,
(c) a solvent consisting of a cyclic N—(C$_1$-C$_6$ alkyl) amide, the cyclic amide being used in a molar proportion of at least 1 with respect to the alkyl formate whereby the cyclic N—(C$_1$-C$_6$ alkyl) amide aids in providing good selectivity of the R—CHO.

2. Process according to claim 1, in which the operational temperature is 150° to 230° C.

3. Process according to claim 2, in which the operational temperature is 160° to 200° C.

4. Process according to claim 1, in which the CO pressure is at least 1 MPa.

5. Process according to claim 4, in which the CO pressure is at least 5 MPa.

6. Process according to claim 1, in which the catalyst is based on a metal selected from Rh, Ru, Ir and mixtures of them.

7. Process according to claim 1, in which the promoter is selected from an alkali metal iodide, an alkaline earth metal iodide, a quaternary ammonium iodide and a phosphonium iodide.

8. Process according to claim 1, in which the promoter is a mixture of an alkali metal iodide and chromium hexacarbonyl.

9. Process according to claim 1, in which the promoter is a mixture of a covalent compound of iodine selected from iodine and a C$_1$-C$_4$ alkyl iodide or hydriodic acid with a phosphine or a tertiary amine.

10. Process according to claim 9, in which the molar concentration of triphenylphosphine is at least equal to the molar concentration of the covalent compound of iodine.

11. Process according to claim 1, in which the CO is provided by a gas exhausted from a steelmaking plant.

12. The process according to claim 1 wherein the cyclic N—(C$_1$-C$_6$ alkyl) amide solvent can be selected from the group consisting of N-methylpyrrolidone, N-ethylpyrrolidone and N,N-dimethylimidazolidinone.

* * * * *